(12) United States Patent
Goede

(10) Patent No.: US 10,150,153 B1
(45) Date of Patent: Dec. 11, 2018

(54) SYSTEMS AND METHODS TO AXIALLY ALIGN DIES

(71) Applicant: Ridge Tool Company, Elyria, OH (US)

(72) Inventor: Brendon Goede, Avon, OH (US)

(73) Assignee: Ridge Tool Company, Elyria, OH (US)

( * ) Notice: Subject to any disclaimer, the term of this patent is extended or adjusted under 35 U.S.C. 154(b) by 0 days.

(21) Appl. No.: 15/865,753

(22) Filed: Jan. 9, 2018

(51) Int. Cl.
| | |
|---|---|
| *B21D 37/10* | (2006.01) |
| *B21D 37/12* | (2006.01) |
| *B21D 39/04* | (2006.01) |
| *H01R 43/042* | (2006.01) |
| *H01R 43/058* | (2006.01) |
| *A61C 7/04* | (2006.01) |
| *B25B 7/02* | (2006.01) |

(52) U.S. Cl.
CPC ............ *B21D 37/12* (2013.01); *A61C 7/04* (2013.01); *B21D 39/04* (2013.01); *B21D 39/046* (2013.01); *B21D 39/048* (2013.01); *H01R 43/042* (2013.01); *H01R 43/058* (2013.01); *B25B 7/02* (2013.01)

(58) Field of Classification Search
CPC .... B21D 37/12; B21D 39/046; B21D 39/048; B21D 37/10; H01R 43/042; H01R 43/048; B25B 7/02
USPC ...................................................... 72/409.19
See application file for complete search history.

(56) References Cited

U.S. PATENT DOCUMENTS

| | | | | |
|---|---|---|---|---|
| 2,853,908 | A | * | 9/1958 | Logan ................ H01R 43/042 |
| | | | | 72/404 |
| 4,027,519 | A | * | 6/1977 | Bachle ............... H01R 43/058 |
| | | | | 29/517 |
| 4,198,748 | A | | 4/1980 | Lewis |
| 4,292,833 | A | | 10/1981 | Lapp |
| 5,138,864 | A | * | 8/1992 | Tarpill ............... H01R 43/042 |
| | | | | 29/751 |
| 5,267,464 | A | | 12/1993 | Cleland |
| 5,421,186 | A | | 6/1995 | Lefavour |
| 5,775,158 | A | | 7/1998 | Hensley et al. |
| 6,125,682 | A | | 10/2000 | Rzasa et al. |
| 6,779,575 | B1 | | 8/2004 | Arthun |
| 7,237,427 | B2 | | 7/2007 | Viegener |
| 7,967,602 | B2 | * | 6/2011 | Lindquist ................ A61C 7/04 |
| | | | | 140/106 |
| 9,166,353 | B1 | | 10/2015 | Doornbos |
| 9,808,851 | B2 | * | 11/2017 | Thorson ............... B21D 39/04 |

* cited by examiner

*Primary Examiner* — David B Jones
(74) *Attorney, Agent, or Firm* — Mark E. Bandy; Rankin, Hill & Clark LLP

(57) ABSTRACT

Die sets and tools using such die sets, are described which promote axial alignment of the dies during die closure. In addition, jaw sets for tools are described that promote axial alignment of the jaws during die closure. Also described are related methods using the die sets and/or tools with such die sets.

22 Claims, 6 Drawing Sheets

SYSTEMS AND METHODS TO AXIALLY ALIGN DIES

FIELD

The present subject matter relates to systems and methods to axially align dies and/or jaws of a tool and particularly during a working cycle of the tool. In particular, the present subject matter relates to die sets and crimping tools that utilize alignment provisions.

BACKGROUND

Crosslinked polyethylene tubing (PEX) is widely used in plumbing applications for transporting potable water. In such systems, connections are typically made using fittings that are crimped in place by a crimp tool. Most fitting systems are radial press systems. A seal is created by inwardly compressing the PEX tubing over a barbed male component or other component such as a union, T-adapter, manifold, or valve. A ring or sleeve is positioned over the tubing and permanently deformed around the entire circumference of the tubing using the crimp tool to create a compressive seal between the tubing and the component. Thus, the crimp tool engages the ring radially and the crimp profile formed in the ring results from the tool. An example of these systems are those that satisfy the ASTM F1807 crimp standard.

Although satisfactory in many respects, crimped connections may exhibit dimensional variations in the circumferential crimped regions or bands formed in the ring or sleeve. In many instances, an axial variability may exist in which one portion of a crimped region is not aligned or "matched" with an adjacent portion of the crimped region. Thus, one portion of the crimped region may appear to be axially "shifted" relative to its adjacent portion.

Another dimensional variation that may exist in a crimped connection is in the diameter of the crimped region. In particular, diametric dimension repeatability may be poor from one crimp to another crimp.

Both of these problems, i.e., axial variability of crimps and diametric dimension repeatability between crimps, can result from poor axial alignment between the dies of the crimp tool. Accordingly, a need exists for methods and provisions to axially align dies and thereby reduce the potential for occurrence of the noted problems.

SUMMARY

The difficulties and drawbacks associated with previous approaches are addressed in the present subject matter as follows.

In one aspect, the present subject matter provides a die set comprising a first die defining a proximal end, a distal end, and at least one circumferential crimping surface extending between the proximal end and the distal end. The die set also comprises a second die defining a proximal end, and distal end, and at least one circumferential crimping surface extending between the proximal end and the distal end. The first die and the second die are positionable within a crimping plane between an opened position and a closed position. The closed position occurs upon the distal end of the first die contacting the distal end of the second die and the circumferential crimping surface of the first die and the circumferential crimping surface of the second die forming a closed circular crimp or substantially circular region. The distal end of the first die includes a male projection extending in a direction in the crimping plane, and the distal end of the second die includes a female receiving region defined along the distal end of the second die. The female receiving region is sized and shaped to fittingly engage the male projection at the closed position of the first die and the second die.

In another aspect, the present subject matter provides a tool system comprising a tool having an actuator, and a jaw assembly including a first jaw and a second jaw. The first jaw and the second jaw are positionable within a crimping plane between an opened position and a closed position. The tool system also comprises a die set adapted for placement and engagement between the first jaw and the second jaw. The die set includes a first die having a proximal end and a distal end, and a second die having a proximal end and a distal end. The distal end of the first die includes a first male projection extending in a direction in the crimping plane, and the distal end of the second die includes a female receiving region defined along the distal end of the second die. The female receiving region is sized and shaped to fittingly engage the male projection at the closed position of the first die and the second die.

In yet another aspect, the present subject matter provides a method to axially align a first die and a second die used in a jaw assembly positionable between an opened position and a closed position. The method comprises forming alignment provisions in a distal end of the first die, and forming alignment provisions in a distal end of the second die.

As will be realized, the subject matter described herein is capable of other and different embodiments and its several details are capable of modifications in various respects, all without departing from the claimed subject matter. Accordingly, the drawings and description are to be regarded as illustrative and not restrictive.

DETAILED DESCRIPTION OF THE EMBODIMENTS

The present subject matter relates to tools and/or tool systems that include a crimp or press tool with a selectively positionable jaw assembly and one or more die sets that can be used with the tool to crimp or deform a variety of fittings. In many embodiments, the die sets are insertable and/or removable with regard to the tool.

In one aspect, the subject matter provides die sets and/or jaws which are configured to axially align during closure of the dies and/or jaws, i.e., during a working cycle. In another aspect, the subject matter provides methods for axially aligning a die set or jaws during a working cycle such as a crimping or pressing operation.

Figure 1:
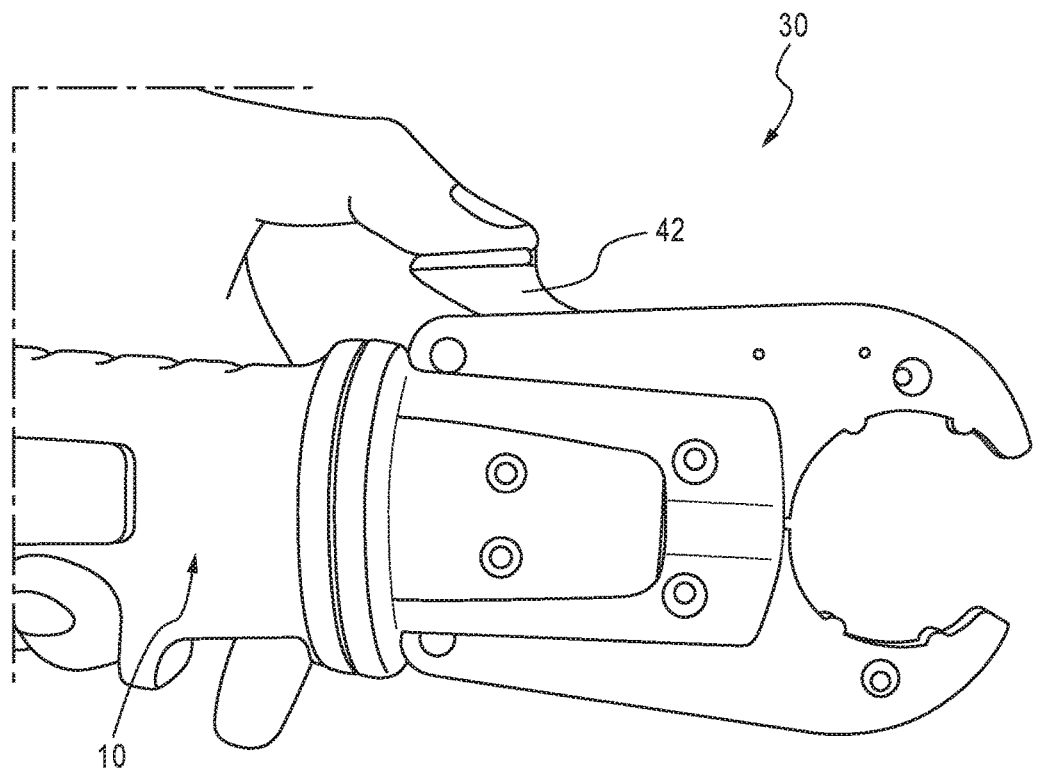
FIG. 1 illustrates a user holding an embodiment of a tool in accordance with the present subject matter, and depicts the tool and its jaw assembly.

The tools are typically electrically powered and in many embodiments utilize an actuator assembly having a roller screw assembly which upon activation, displaces a ram member which in turn actuates a jaw assembly. FIG. 1 illustrates a tool 10 having a jaw assembly 30 which can be selectively opened and closed as described herein. Typically, the jaw assembly 30 can be attached to, and removed from the tool 10. However, the present subject matter includes crimping tools in which the jaw assembly 30 is generally not disengageable from the tool 10. Furthermore, although in many embodiments the crimping tool is electrically powered, the present subject matter also includes tools that are hydraulically powered, pneumatically powered, and/or manually powered. Moreover, although the crimping tool 10 is described as utilizing a roller screw assembly, it will be understood that the present subject matter includes tools utilizing a variety of mechanisms for powering or advancing a ram member and/or closing the jaw assembly. Although the present subject matter tools are typically battery powered, it will be understood that the tools can include cords for transmitting electrical power to the tool. Such corded tools would typically not include a battery. Alternatively, such battery-free tools may simply include a port or other receptacle at which electrical power is provided.

Figure 2:
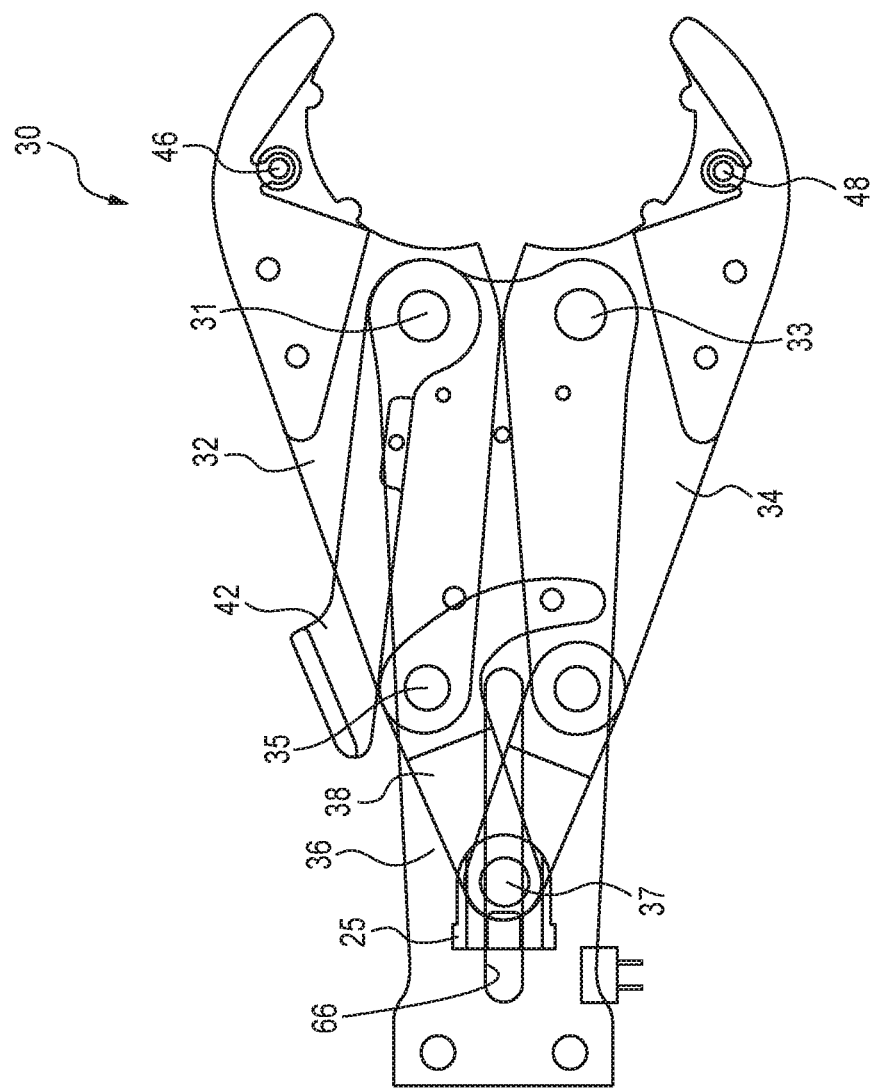
FIG. 2 is a schematic illustration of the jaw assembly of the tool of FIG. 1 showing the jaws in an open position.

Referring to FIG. 2, a schematic partial cross sectional view of an embodiment of a jaw assembly 30 in accordance with the present subject matter is illustrated. FIG. 2 illustrates a jaw assembly 30 comprising a first jaw 32, a second jaw 34, and a jaw frame 36 to which each jaw 32, 34 is pivotally coupled by jaw pins 31 and 33, respectively. The jaw assembly 30 also comprises a linkage assembly that includes a cam linkage member 38 which is pivotally affixed to the jaw 32 by a jaw pin 35, and pivotally affixed to a clevis assembly 25 by a jaw pin 37. The clevis 25 is linearly displaced along or within a guide slot 66 upon actuation of a motor and roller screw assembly (not shown). The guide slot 66 is defined within one or more frame members such as the frame member 36 of the jaw assembly 30.

In many embodiments, the jaw assembly 30 also comprises a lever 42 that is pivotally supported at the jaw pin 31 of the first jaw 32. The lever 42 is positioned and configured to selectively contact a region of the cam linkage member 38, as described in greater detail herein. After performing a crimping or clinching operation such that the jaws 32, 34 are in a closed position, a user can easily open the jaws 32, 34 by pressing the lever 42. Pressing the lever 42, applies a rotational moment to the cam linkage member 38, which in turn linearly displaces the clevis 25 to move away from the jaws 32, 34, thereby opening the jaws. A user can grip a workpiece such as plastic tubing and/or a fitting with one hand and engage the fitting with the tool to complete the crimp with the other hand. A typical hand position when operating a tool 10 in accordance with the present subject matter is depicted in FIG. 1 with a user's thumb positioned on the lever 42 and forefinger at a trigger position or other convenient location. As shown in FIGS. 1 and 2, a user's thumb can be used to depress the lever 42, rotate the cam linkage member 38 about the cam pivot pin 35, and open the jaws 32, 34 to engage a fitting (not shown) before a crimp or clinch is made. A lever spring biases the lever 42 so that contact is maintained between the cam linkage member 38 and the lever 42 through a range of travel of the jaw 32. It will be appreciated that the present subject matter tools can utilize a wide array of other biasing members to bias the lever 42, instead of or in addition to the lever spring. Furthermore, it will be understood that the present subject matter includes jaw assemblies that are free of any such biasing member(s).

In many embodiments, the jaw assembly such as jaw assembly 30 shown in FIG. 2 includes one or more protruding members 46, 48 that project from a working face of one or both jaws, preferably both jaws, and which are configured to engage corresponding recesses or receiving regions in one or more die sets, described herein. In a particular version, the jaw 32 includes a plurality of such protruding members 46, and the jaw 34 includes a plurality of such protruding members 48. In certain embodiments, each jaw includes two protruding members each extending from opposite faces of the jaw. The protruding members provide support for the die sets to react against forces exerted on the dies during a crimping operation. In a particularly preferred version, the protruding members 46, 48 are configured to react exclusively against all forces exerted on the dies during a crimping operation and thus no such forces are exerted upon a pin(s) or other retaining member(s) utilized to attach or affix the dies to the jaws 32, 34 in an unloaded state.

Additional details and description of the tool 10, the jaw assembly 30, and operation of the tool 10 and jaw assembly 30 are provided in US applications U.S. Ser. No. 15/379,105 filed Dec. 14, 2016; and U.S. Ser. No. 15/429,978 filed Feb. 10, 2017. It will be appreciated that in no way is the present subject matter limited to the particular tool 10 and/or the jaw assembly 30 described and illustrated. Instead, the present subject matter includes the use of a variety of different tools and/or jaw assemblies.

Each die of a two-die set includes one or more engagement profile(s) that is matched with one or more corresponding profile(s) in the other die. Typically, male and female features are provided along a profile or portion thereof in each die such that as the dies approach closure and contact each other, the male and female features engage each other in such a manner that the dies are axially aligned and/or precluded from axial movement relative to each other. In addition, provision of such features in a die set and use of the die set for crimping has been found to reduce occurrence of problems associated with axial variability and/or diametric dimension repeatability. Provision of such features in a die set and use of the die set for crimping has been found to produce crimps or crimped regions that are aligned with each other.

Figure 3:
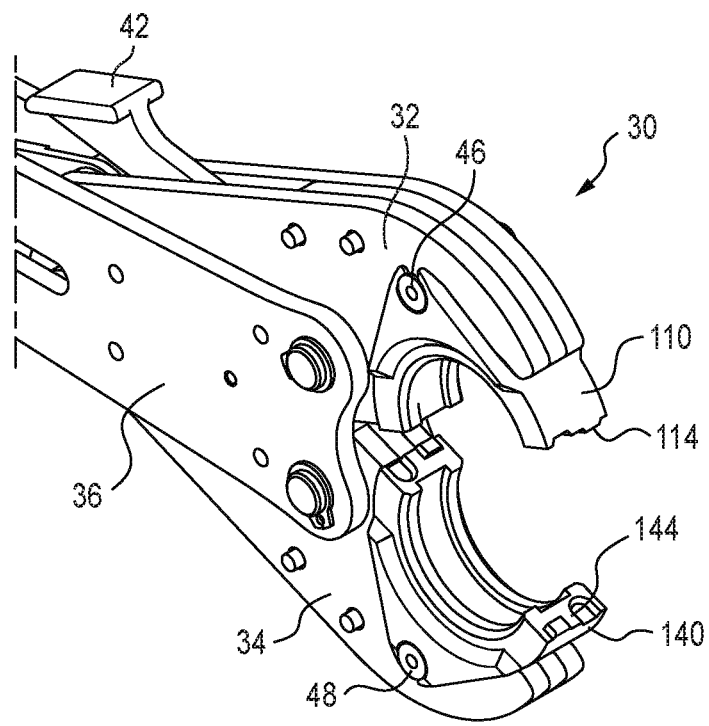
FIG. 3 is a partial perspective view of a tool and jaw set having a pair of dies in accordance with the present subject matter positioned at a fully open state.
Figure 4:
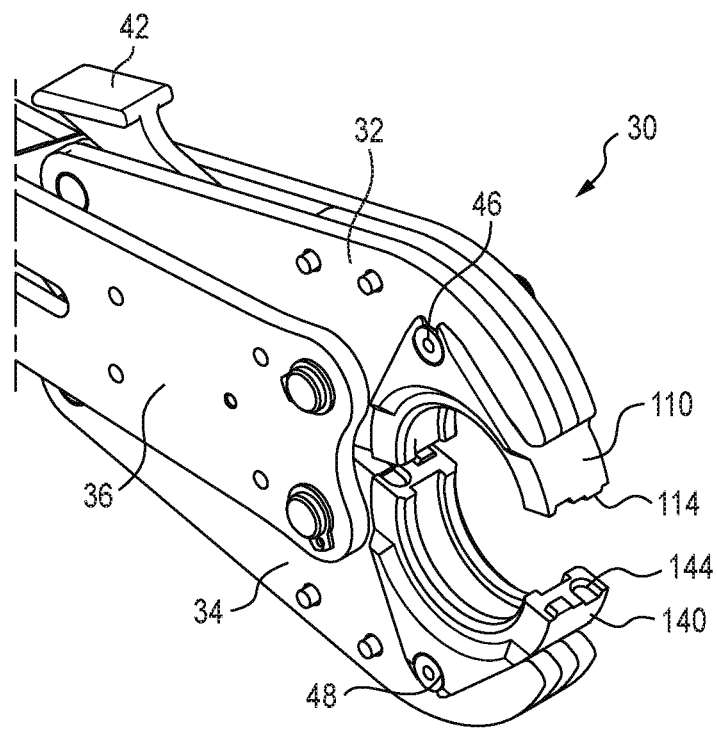
FIGS. 4-6 are partial perspective view of the tool, jaw set, and dies shown in FIG. 3 as the dies are moved toward a closed position.
Figure 5:
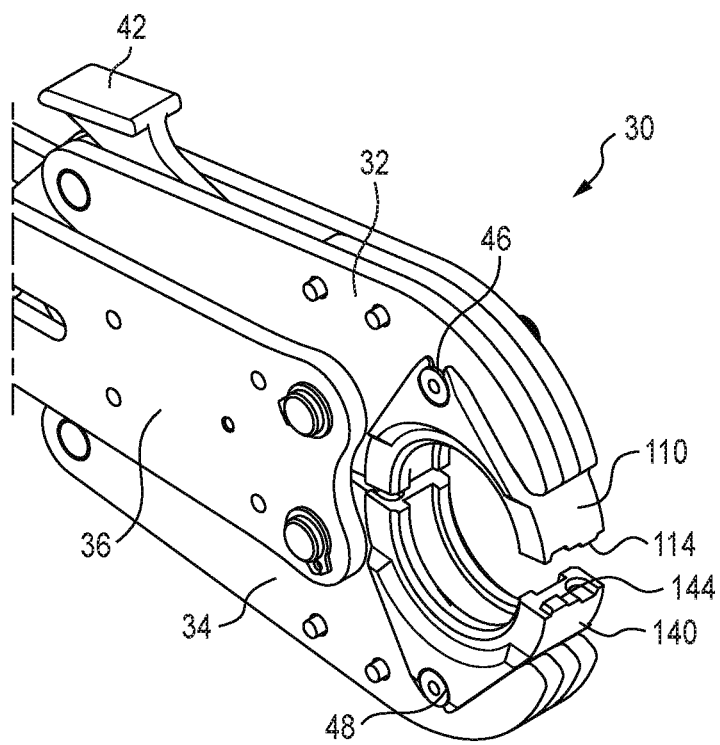
Figure 6:
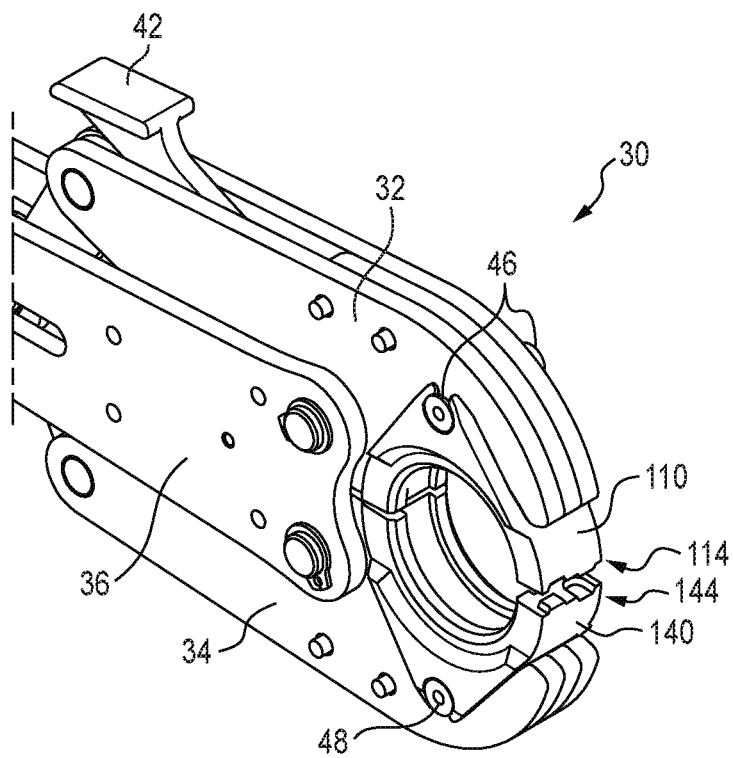
Figure 7:
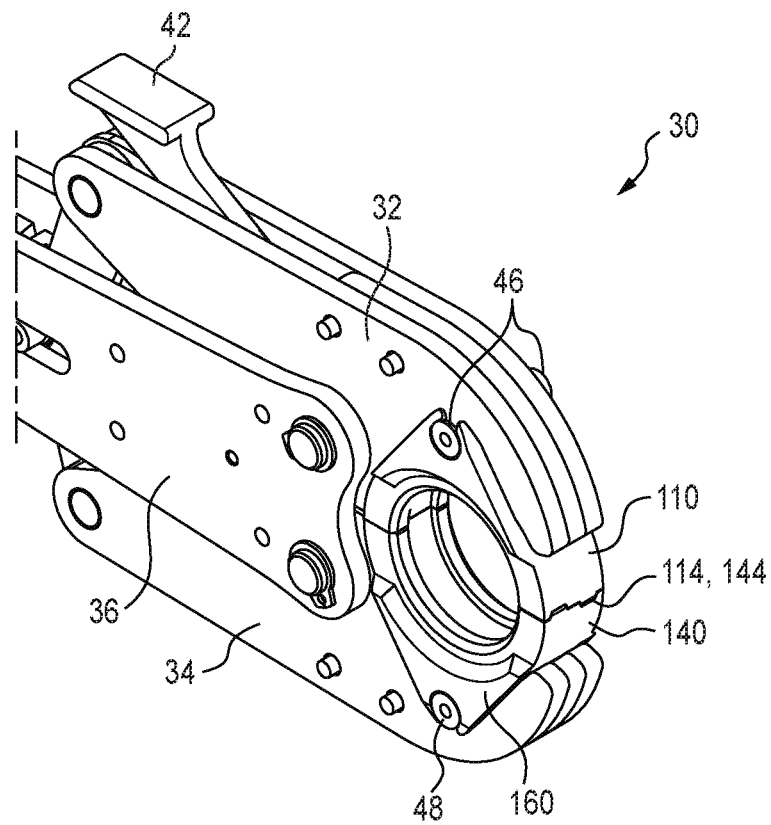
FIG. 7 is a partial perspective view of the tool, jaw set, and dies of FIGS. 3-6 showing the dies at a closed position.

FIGS. 3-7 illustrate an embodiment of the dies in a jaw set 30 in association with a typical crimping tool (not shown), and positioning the dies from a fully opened position depicted in FIG. 3 to a closed position shown in FIG. 7. Specifically, the dies are depicted as dies 110 and 140 and are engaged in the jaws 32, 34 of the tool. A first die 110 is shown engaged with the first jaw 32, and the second die 140 is shown engaged with the second jaw 34. It will be understood that the present subject matter includes arrangements in which the second die 140 is engaged with the first jaw 32, and the first die 110 is engaged with the second jaw 34. As explained in greater detail herein, each die includes a distal end which is the end or region of the die located at the outermost end or region of the jaws, typically farthest from the tool. And, each die includes a proximal end or region which is generally opposite the distal end. In the embodiment depicted in FIGS. 3-7, the first die 110 has a distal end 114, and the second die 140 has a distal end 144. As will be understood, the jaws 32, 34 are positionable within a crimping plane between a fully opened position such as depicted in FIG. 3, and a closed position as shown in FIG. 7. The crimping plane is typically defined as a plane bisecting jaws 32, 34 and extending parallel or coplanar with the jaws and their major axes. Reference to a fully closed position of the dies and/or jaws as noted herein, occurs upon full contact and engagement between dies incorporated in the jaw assembly. Typically, a fully closed position of the jaws occurs upon the distal end 114 of the first die 110 contacting the distal end 144 of the second die 140, and/or the circumferential crimping surface 116 of the first die 110 and the circumferential crimping surface 146 of the second die 140 forming a closed circular or substantially circular crimp region. It will be understood that the dies form a crimp region that is circular or substantially circular. The term "substantially circular" as used herein refers to a shape that is approximately circular. In many embodiments, the term "substantially circular" refers to a shape similar to that of a circle in which a maximum span or distance of the shape is within a range of from about 101% to about 120% of a minimum span or distance of the shape.

Figure 8:
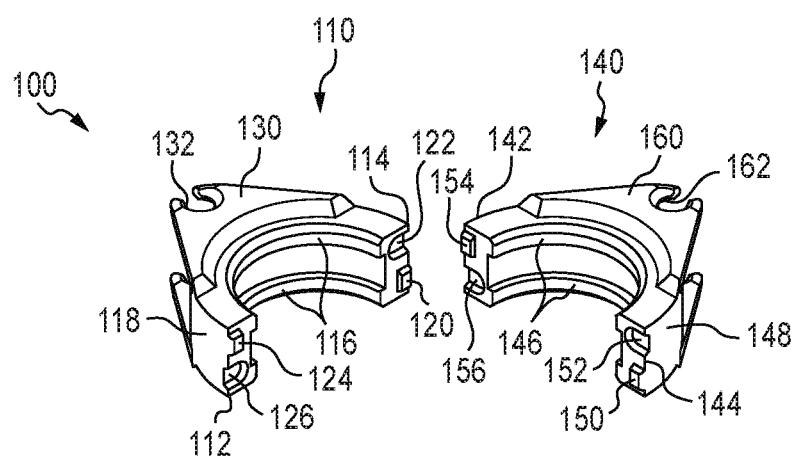
FIG. 8 is a perspective view showing an embodiment of a die in accordance with the present subject matter.

FIG. 8 is a perspective view of the die set 100 and dies 110 and 140 in accordance with the present subject matter. The dies 110 and 140 are shown in isolation and removed from the tool and jaws 32, 34, for convenience in describing various features of the dies. The first die 110 includes the previously noted distal end 114, and an opposite proximal end 112. One or more circumferential crimping surfaces 116 extend generally between the ends 112, 114 of the die 110. An outer periphery 118 also extends between the ends 112, 114. The die 110 includes along the distal end 114 a first male projection 120 and a first female receiving region 122. In certain embodiments, the die 110 may additionally include along the proximal end 112, a second male projection 124 and a second female receiving region 126. And in particular embodiments, the die 110 includes one or more engagement members 130, each of which defines a receiving slot 132. The receiving slot 132 is sized and shaped to engage a protruding member of the corresponding jaw, such as protruding member 46 of the jaw 32.

The second die 140 includes the previously noted distal end 144, and an opposite proximal end 142. One or more circumferential crimping surfaces 146 extend generally between the ends 142, 144 of the die 140. An outer periphery 148 also extends between the ends 142, 144. The die 140 includes along the distal end 144, a first male projection 150 and a first female receiving region 152. In certain embodiments, the die 140 may also include along the proximal end 142, a second male projection 154 and a second female receiving region 156. And, in certain embodiments, the die 140 includes one or more engagement members 160, each of which defines a receiving slot 162. The slot 162 is sized and shaped to engage a protruding member of the corresponding jaw, such as protruding member 48 of the jaw 34.

The male projections of the dies, i.e., male projections 120, 124, 150, and 154, are oriented such that upon installation of the dies 110, 140 in the jaws 32, 34; each male projection extends in a direction or parallel to, the previously noted crimping plane. However, it will be appreciated that the present subject matter includes other orientations and/or configurations of the male projections.

In particular versions of the present subject matter, one or more of the female receiving region(s) are sized and shaped to fittingly engage a corresponding male projection. Specifically, the first female region 152 of the second die 140 is sized and shaped to fittingly engage the first male projection 120 of the first die 110. And, the first female region 122 of the first die 110 is sized and shaped to fittingly engage the first male projection 150 of the second die 140. If alignment provisions are utilized on the proximal ends of the dies, a second female region 156 of the second die 140 is sized and shaped to fittingly engage the second male projection 124 of the first die 110. And, the second female region 126 of the first die 110 is sized and shaped to fittingly engage the second male projection 154 of the second die 140.

In certain versions of the present subject matter, the circumferential crimping surfaces of the die(s) are free of any alignment provisions. Thus, for example, the circumferential crimping surfaces 116 of the first die 110 are free of the male projection(s) 120, 124, and the female receiving regions 122, 126. And, the circumferential crimping surfaces 146 of the second die 140 are free of the male projection(s) 150, 154, and the female receiving regions 152, 156.

Figure 9:
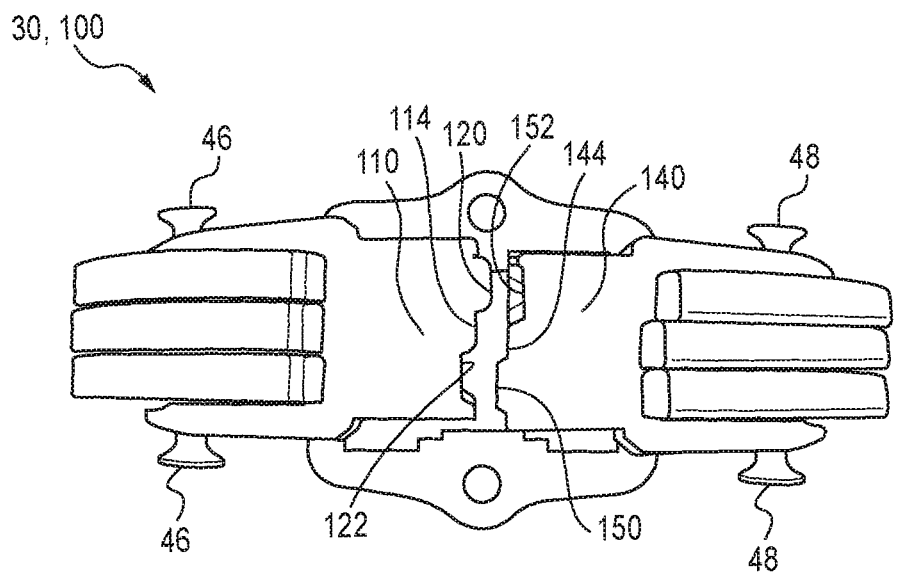
FIGS. 9 and 10 are end views showing distal ends and engagement provisions of dies in accordance with the present subject matter.
Figure 10:
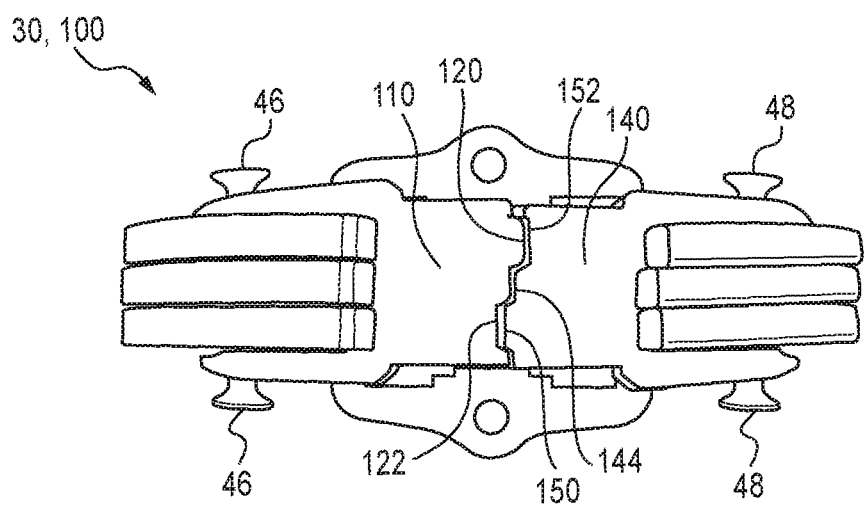

FIGS. 9 and 10 show an embodiment of the die set 100 incorporated in the jaw assembly 30, in which the die set is configured to axially align during a working operation. FIG. 9 illustrates misalignment of the dies prior to closure. As the dies 110, 140 are moved toward closure, their engagement profiles result in alignment, and particularly axial alignment, of the dies at a fully closed position as shown in FIG. 10. Alignment occurs due to the particular engagement profile of male and female features in each die.

The present subject matter also includes tools, jaws, and/or jaw components that utilize and include the alignment provisions. Thus for example, distal ends of a pair of jaws could include the alignment provisions described herein. Incorporation of the alignment provisions in jaws enables conventional die sets free of alignment provisions to be used with the jaws, and still achieve aligned crimping or pressing as described herein.

The present subject matter also includes die sets comprising more than two (2) dies. That is, the subject matter includes die sets having a total number of dies within a range of 2 to 10 or more.

The present subject matter also provides methods for axially aligning dies when incorporated in a positionable jaw set as described herein. The methods involve forming alignment provisions in corresponding regions of the dies. Typically, this involves forming alignment provisions in a distal end of a first die and also forming alignment provisions in a distal end of a second die. The alignment provisions can take a variety of forms. However, in many embodiments, the alignment provisions include a male projection along a distal end of the first die and a female receiving region along a distal end of the second die. The alignment provisions may also include a male projection along a distal end of the second die and a female receiving region along a distal end of the first die. The male projection(s) and female receiving region(s) are as described herein. The methods may in certain versions also include forming such structures and features along proximal ends of the dies. And, it will be understood that the present subject matter includes forming such features and/or structures in engagement end regions of jaws rather than dies.

In accordance with the present subject matter, it has been discovered that use of the dies, and/or jaws, and/or methods as described herein significantly reduces the amount of axial variability observed from crimp band to crimp band, along with reducing the overall variability of the crimp. In addition, use of the dies and/or jaws as described herein significantly improves the diametric dimension repeatability from crimp to crimp. A direct result of the crimp bands being misaligned is significant diameter differences between the inner and outer bands. By implementing the features of the embodiments described herein, the inner and outer band consistency improves dramatically.

Many other benefits will no doubt become apparent from future application and development of this technology.

All patents, applications, standards, and articles noted herein are hereby incorporated by reference in their entirety.

The present subject matter includes all operable combinations of features and aspects described herein. Thus, for example if one feature is described in association with an embodiment and another feature is described in association with another embodiment, it will be understood that the present subject matter includes embodiments having a combination of these features.

As described hereinabove, the present subject matter solves many problems associated with previous strategies, systems and/or devices. However, it will be appreciated that various changes in the details, materials and arrangements of components, which have been herein described and illustrated in order to explain the nature of the present subject matter, may be made by those skilled in the art without departing from the principle and scope of the claimed subject matter, as expressed in the appended claims.

What is claimed is:

1. A die set comprising:
a first die defining a proximal end, a distal end, and at least one circumferential crimping surface extending between the proximal end and the distal end;
a second die defining a proximal end, and distal end, and at least one circumferential crimping surface extending between the proximal end and the distal end;
wherein the first die and the second die are positionable within a crimping plane between an opened position and a closed position, the closed position occurring upon the distal end of the first die contacting the distal end of the second die and the circumferential crimping surface of the first die and the circumferential crimping surface of the second die forming a closed circular or substantially circular crimp region,
wherein the distal end of the first die includes a male projection extending in a direction in the crimping plane, and the distal end of the second die includes a female receiving region defined along the distal end of the second die, the female receiving region sized and shaped to fittingly engage the male projection at the closed position of the first die and the second die;
wherein the male projection and the female receiving region engage each other in such a manner that the first die and the second die are axially aligned and axial movement of one of the die relative to the other die is precluded.

2. A die set comprising:
a first die defining a proximal end, a distal end, and at least one circumferential crimping surface extending between the proximal end and the distal end;
a second die defining a proximal end, and distal end, and at least one circumferential crimping surface extending between the proximal end and the distal end;
wherein the first die and the second die are positionable within a crimping plane between an opened position and a closed position, the closed position occurring upon the distal end of the first die contacting the distal end of the second die and the circumferential crimping surface of the first die and the circumferential crimping surface of the second die forming a closed circular or substantially circular crimp region,
wherein the distal end of the first die includes a male projection extending in a direction in the crimping plane, and the distal end of the second die includes a female receiving region defined along the distal end of the second die, the female receiving region sized and shaped to fittingly engage the male projection at the closed position of the first die and the second die,
wherein the distal end of the first die further includes a female receiving region and the distal end of the second die further includes a male projection extending in a direction in the crimping plane, the female receiving region of the first die sized and shaped to fittingly engage the male projection of the second die at the closed position of the first die and the second die.

3. The die set of claim 1 wherein both a circumferential crimping surface of the first die and a circumferential crimping surface of the second die are free of the male projection and the female receiving region.

4. The die set of claim 1 wherein the proximal end of the first die includes a male projection extending in a direction in the crimping plane, and the proximal end of the second die includes a female receiving region defined along the proximal end of the second die, the female receiving region at the proximal end of the second die sized and shaped to fittingly engage the male projection at the proximal end of the first die at the closed position of the first die and the second die.

5. A die set comprising:
a first die defining a proximal end, a distal end, and at least one circumferential crimping surface extending between the proximal end and the distal end;
a second die defining a proximal end, and distal end, and at least one circumferential crimping surface extending between the proximal end and the distal end;
wherein the first die and the second die are positionable within a crimping plane between an opened position and a closed position, the closed position occurring upon the distal end of the first die contacting the distal end of the second die and the circumferential crimping surface of the first die and the circumferential crimping surface of the second die forming a closed circular or substantially circular crimp region,
wherein the distal end of the first die includes a male projection extending in a direction in the crimping plane, and the distal end of the second die includes a female receiving region defined along the distal end of the second die, the female receiving region sized and shaped to fittingly engage the male projection at the closed position of the first die and the second die,
wherein the proximal end of the first die further includes a female receiving region and the proximal end of the second die further includes a male projection extending in a direction in the crimping plane, the female receiving region at the proximal end of the first die sized and shaped to fittingly engage the male projection at the proximal end of the second die at the closed position of the first die and the second die.

6. The die set of claim 4 wherein both the circumferential crimping surface of the first die and the circumferential crimping surface of the second die are free of the male projection at the proximal end of the first die and the female receiving region at the proximal end of the second die.

7. The die set of claim 1 wherein the first die includes an engagement member defining a receiving slot.

8. The die set of claim 7 wherein the second die includes an engagement member defining a receiving slot.

9. The die set of claim 1 wherein the first die defines two circumferential crimping surfaces extending between the proximal end and the distal end of the first die.

10. The die set of claim 9 wherein the second die defines two circumferential crimping surfaces extending between the proximal end and the distal end of the second die.

11. A tool system comprising:
a tool having an actuator, and a jaw assembly including a first jaw and a second jaw, wherein the first jaw and the second jaw are positionable within a crimping plane between an opened position and a closed position;
a die set adapted for placement and engagement between the first jaw and the second jaw;
wherein the die set includes a first die having a proximal end and a distal end, and a second die having a proximal end and a distal end,
wherein the distal end of the first die includes a first male projection extending in a direction in the crimping plane, and the distal end of the second die includes a female receiving region defined along the distal end of the second die, the female receiving region sized and shaped to fittingly engage the male projection at the closed position of the first die and the second die;
wherein the male projection and the female receiving region engage each other in such a manner that the first die and the second die are axially aligned and axial movement of one of the die relative to the other die is precluded.

12. The tool system of claim 11 wherein the actuator further includes a roller screw assembly.

13. The tool system of claim 11 wherein the actuator includes an electric motor.

14. The tool system of claim 11 wherein the proximal end of the first die includes a male projection extending in a direction in the crimping plane, and the proximal end of the second die includes a female receiving region, the female receiving region at the proximal end of the second die sized and shaped to fittingly engage the male projection at the proximal end of the second die at the closed position of the first jaw and the second jaw.

15. The tool system of claim 11 wherein both of the first die and the second die include a circumferential crimping surface extending between the distal end and the proximal end of each die and both the circumferential crimping surface of the first die and the circumferential crimping surface of the second die are free of the male projection and the female receiving region.

16. The tool system of claim 15 wherein both the circumferential crimping surface of the first die and the circumferential crimping surface of the second die are free of the male projection and the female receiving region at the distal end of the first die and the second die.

17. The tool system of claim 11 wherein the first die includes an engagement member defining a receiving slot.

18. The tool system of claim 17 wherein the second die includes an engagement member defining a receiving slot.

19. The tool system of claim 11 wherein the first die defines two circumferential crimping surfaces extending between the proximal end and the distal end of the first die.

20. The tool system of claim 19 wherein the second die defines two circumferential crimping surfaces extending between the proximal end and the distal end of the second die.

21. A method to axially align a first die and a second die used in a jaw assembly positionable between an opened position and a closed position, the method comprising:
forming alignment provisions in a distal end of the first die; and
forming alignment provisions in a distal end of the second die;
wherein the alignment provisions include male and female features along each die such that as the dies approach the closed position and contact each other, the male and female features engage each other such that the dies are axially aligned and precluded from axial movement relative to each other.

22. A method to axially align a first die and a second die used in a jaw assembly positionable between an opened position and a closed position, the method comprising:
forming alignment provisions in a distal end of the first die; and
forming alignment provisions in a distal end of the second die,
wherein the alignment provisions in the first die include a male projection and a female receiving region, and the alignment provisions in the second die include a male projection and a female receiving region, the female receiving region of the first die sized and shaped to fittingly engage the male projection of the second die at the closed position of the jaw assembly, and the female receiving region of the second die sized and shaped to fittingly engage the male projection of the first die at the closed position of the jaw assembly.

* * * * *